US008868166B2

(12) United States Patent
Muessig et al.

(10) Patent No.: US 8,868,166 B2
(45) Date of Patent: Oct. 21, 2014

(54) ARRHYTHMIA DETECTION BASED ON ACTIVE MUSCLE NOISE DETECTION

(75) Inventors: Dirk Muessig, West Linn, OR (US); J. Christopher Moulder, Portland, OR (US); Hannes Kraetschmer, West Linn, OR (US); Jeffrey A. Von Arx, Lake Oswego, OR (US); Larry Stotts, Tigard, OR (US)

(73) Assignee: Biotronik SE & Co. KG, Berlin (DE)

( * ) Notice: Subject to any disclaimer, the term of this patent is extended or adjusted under 35 U.S.C. 154(b) by 353 days.

(21) Appl. No.: 13/455,131

(22) Filed: Apr. 25, 2012

(65) Prior Publication Data

US 2012/0283589 A1 Nov. 8, 2012

Related U.S. Application Data

(60) Provisional application No. 61/481,765, filed on May 3, 2011.

(51) Int. Cl.
*A61N 5/04* (2006.01)
*A61B 5/00* (2006.01)
*A61B 5/0452* (2006.01)
*A61N 1/05* (2006.01)
*A61B 5/0464* (2006.01)
*A61B 5/046* (2006.01)

(52) U.S. Cl.
CPC . *A61N 1/05* (2013.01); *A61B 5/721* (2013.01); *A61B 5/0452* (2013.01); *A61B 5/0464* (2013.01); *A61B 5/046* (2013.01)
USPC .......................................................... 600/515

(58) Field of Classification Search
USPC .................................. 600/508, 513, 515, 518
See application file for complete search history.

(56) References Cited

U.S. PATENT DOCUMENTS

| 6,347,245 | B1 | 2/2002 | Lee et al. |
| 2008/0269813 | A1 | 10/2008 | Greenhut et al. |
| 2010/0312131 | A1 | 12/2010 | Naware et al. |

FOREIGN PATENT DOCUMENTS

WO   2008/137539 A1   11/2008

OTHER PUBLICATIONS

European Search Report, dated Aug. 13, 2012, 7 pages.

*Primary Examiner* — Amanda Patton
(74) *Attorney, Agent, or Firm* — ARC IP Law, PC; Joseph J. Mayo

(57) ABSTRACT

Implantable electromedical device or loop recorders or ILRs that solve the problem of very low arrhythmia detection specificities in, i.e., high number of false positives, based on detection and analysis of external noise, specifically muscle noise surrounding the electromedical device. Embodiments generally employ active detection of lead or device movement that induces signal artifacts indicative of external noise. One or more embodiments may detect lead or device movement through use of a piezoelectric transducer, for example located proximally to the device or in the lead of the electromedical.

20 Claims, 3 Drawing Sheets

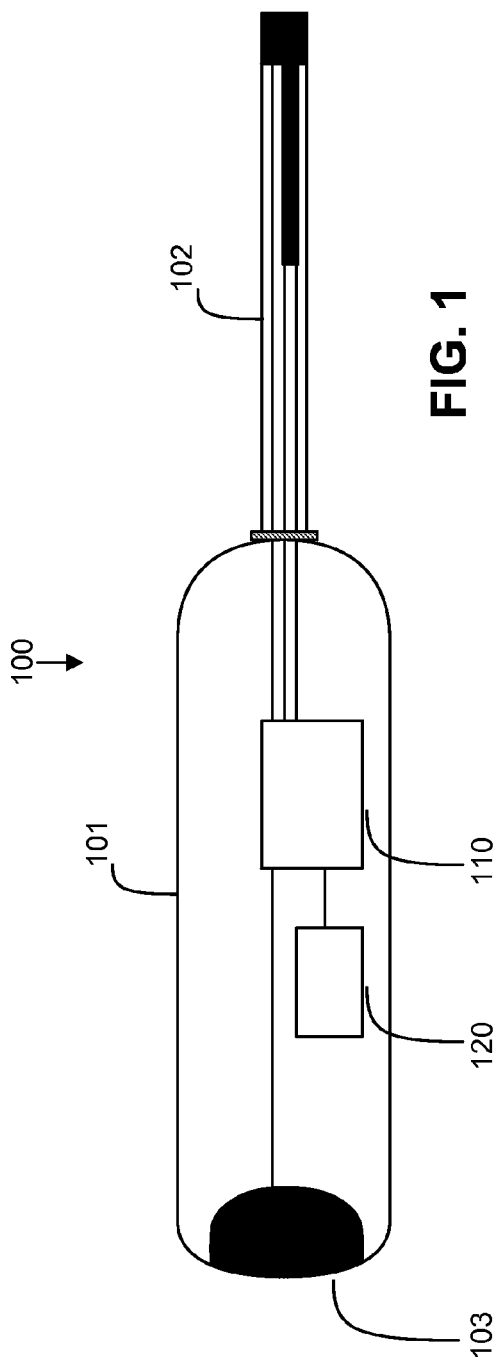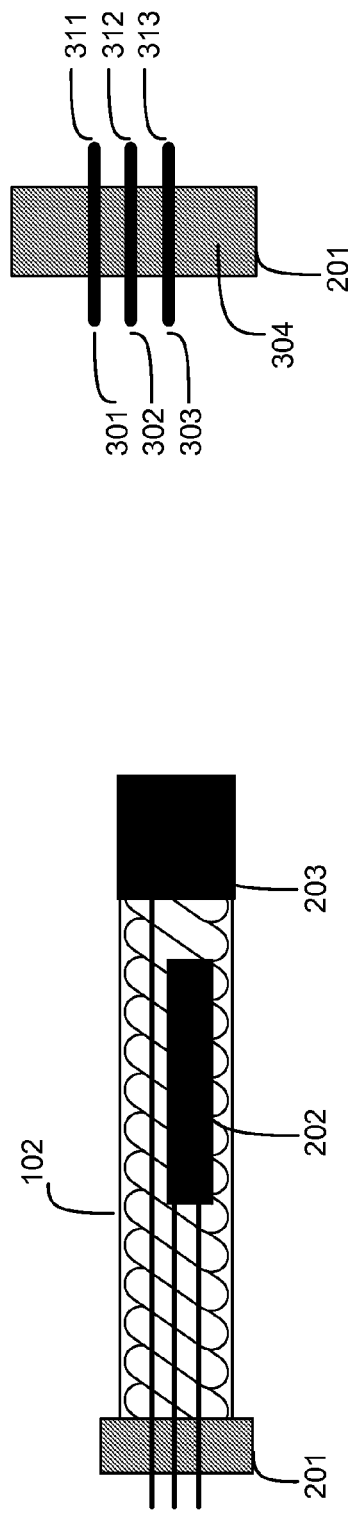

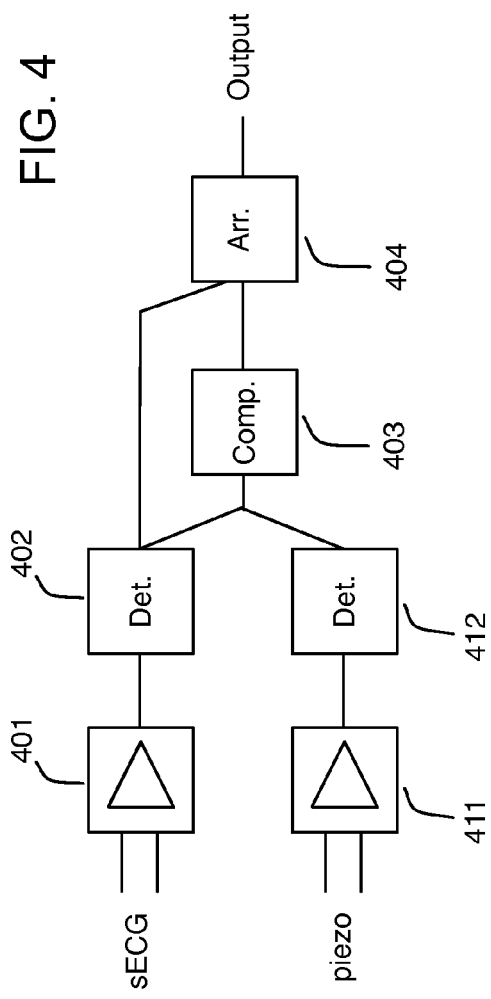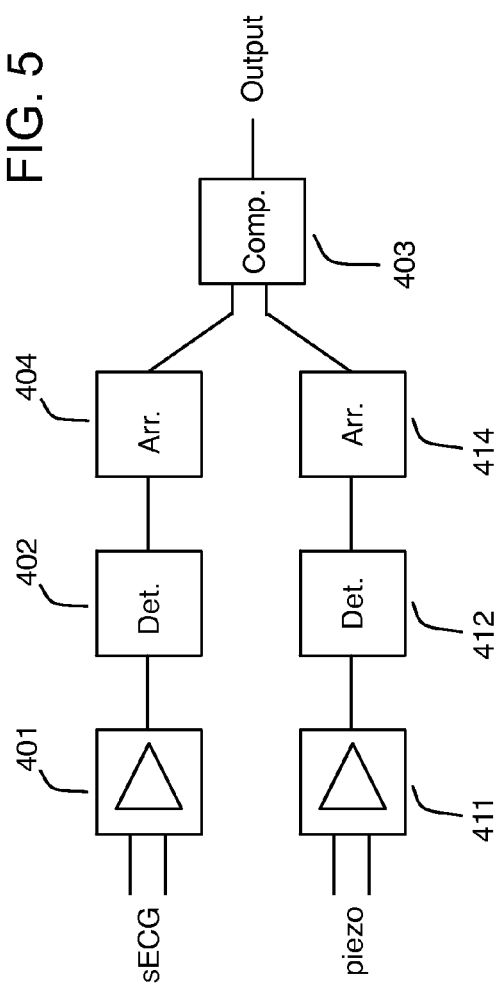

US 8,868,166 B2

ARRHYTHMIA DETECTION BASED ON ACTIVE MUSCLE NOISE DETECTION

This application claims the benefit of U.S. Provisional Patent Application 61/481,765, filed on 3 May 2011, the specification of which is hereby incorporated herein by reference.

BACKGROUND OF THE INVENTION

1. Field of the Invention

Embodiments of the invention relate to an electromedical implant configured to improve arrhythmia detections based on active muscle noise detection, specifically and not by way of limitation, embodiments improve the specificity of the arrhythmia detection by active detection of lead or device movement that induces signal artifacts. The electromedical implant can, for example, be an appropriately configured implantable loop recorder or ILR for long terming monitoring of electrocardiograms or ECGs or other implantable pacemaker or an implantable cardioverter/defibrillator or ICD, or any combination thereof.

2. Description of the Related Art

Arrhythmia detections based on the QRS detection of the subcutaneous ECG or sECG in implantable loop recorders or ILRs are often disturbed by external noise, specifically muscle noise that is generated by a patient, for example due to the movement of the shoulder area of the patient. This noise is can be classified falsely as arrhythmia which for example triggers sECG recordings or alarms to the physician. Existing implantable monitoring systems, such as ILRs have a very low specificity, i.e., high number of false positives, when it comes to arrhythmia detections such as high ventricular rate or atrial fibrillation. Recent studies reported an overall specificity of ILRs of about 15%, with a worst-case specificity for the detection of high ventricular rates of 0.3%. Several reasons have been identified, starting from very small subcutaneous ECG signals to the induction of noise generated by moving artifacts. Existing solutions are very limited and generally attempt to suspend arrhythmia detection in case of high amplitude/high frequency noise. Although such approaches may slightly improve the overall specificity, the problem of "rhythmic noise" artifacts occurring approximately every second to ~5×/second cannot be identified and filtered out using known techniques, for example that are unable to identify this type of noise. "Rhythmic noise" is typically generated in muscle surrounding the ILR, which is related to arm and shoulder movements of the patient (e.g. climbing up stairs, walking/running, or brushing teeth).

BRIEF SUMMARY OF THE INVENTION

Embodiments of the invention may be implemented with implantable loop recorders or ILRs (or other implantable devices) that solve the problem of very low arrhythmia detection specificities in, i.e., high number of false positives, based on detection and analysis of external noise, specifically muscle noise surrounding the ILR. Embodiments of the invention employ active detection of lead or device movement that induces signal artifacts indicative of external noise. One or more embodiments may detect lead or device movement through use of a piezoelectric transducer, for example located proximally to the device or in the lead of the ILR.

Piezoelectric transducers generate a voltage based on vibrations or movement that cause the deformation of a piezoelectric capacitor. The generated voltage is analyzed for coherency with respect to detected QRS complexes of the sECG. If both signal streams have a high similarity, the detected episode is either flagged or otherwise indicated as questionable or may be saved in memory for statistical analysis of specificity and/or ignored and deleted from the arrhythmia statistics, for example not saved in memory of the ILR. Embodiments of the invention thus greatly increase the specificity of arrhythmia detection.

BRIEF DESCRIPTION OF THE DRAWINGS

FIG. 1: illustrates an ILR having a device body and a flexible lead.

FIG. 2: illustrates a close-up of the flexible lead body having a piezoelectric transducer embedded into the lead body. The transducer is connected to the signal analysis module via a feedthrough. The feedthrough also connects the sECG electrode that is e.g. located at the distal end of the lead to the signal analysis module.

FIG. 3: illustrates a close-up of the feedthrough that provides electrical connection of the transducer and sECG lead to the signal analysis module.

FIG. 4: illustrates a logical processing schematic of one embodiment of the signal analysis element or module employed by one or more embodiments of the invention. The signal or data streams from the piezoelectric transducer and the sECG, i.e., the sECG signal and the piezo signal respectively, are routed into different detection modules that generate peak markers or detect signal features. The time sequence of the peak markers or signal features are analyzed for coherency in the comparator element or module, the result of the analysis is forwarded to the arrhythmia element or module for further processing.

FIG. 5: illustrates a logical processing schematic of another embodiment of the signal analysis module employed by one or more embodiments of the invention. In this sequence both signal streams, the sECG signal and the piezo signal, are processed by the arrhythmia detection module simultaneously, or in a time division multiplexed manner, using hardware and/or software and/or firmware or any other processing element. The output is then analyzed by the comparator element or module for concurrent arrhythmia detection.

DETAILED DESCRIPTION OF THE INVENTION

Figure 6:
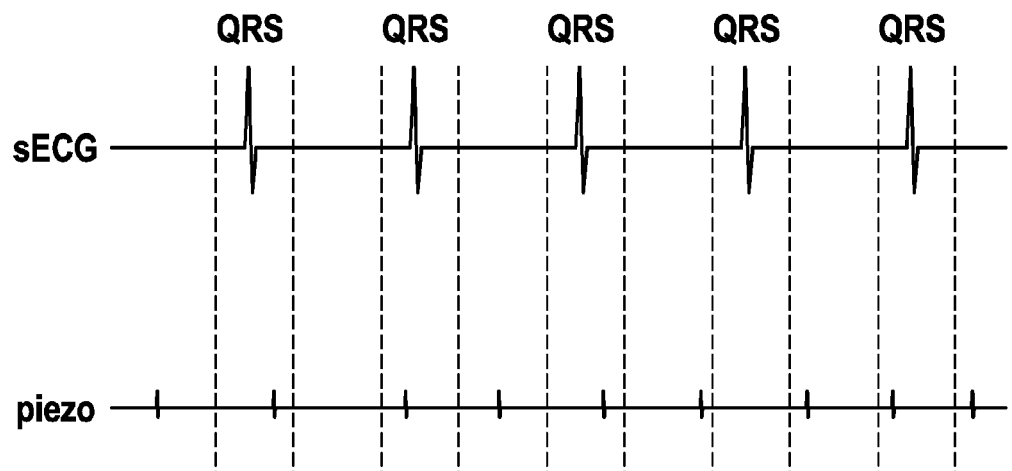
FIG. 6: illustrates an example of correct arrhythmia detection, wherein the sECG signal and the piezo signal are non-coherent.

Embodiments of the invention solve the problem of very low arrhythmia detection specificities in, i.e., high number of false positives, based on detection and analysis of external noise, specifically muscle noise surrounding the implantable loop recorder or ILR. Embodiments of the invention employ active detection of lead or device movement that induces signal artifacts indicative of external noise. For example, one or more embodiments of the invention implement a sensor into the lead that generates a signal when the lead is moving or bending due to muscle activity. One embodiment of the sensor that may be utilized to generate the "muscle activity signal" may be a piezoelectric transducer. Muscle activity surrounding the transducer causes deformation of a piezoelectric capacitor and thereby generates a voltage. This voltage is correlated or otherwise compared in any manner desired to the sECG signal. If both signal streams are coherent, or for example correlate to within a predefined range or threshold, or for example have X piezo events within predefined windows in common within N sECG events, then a detected arrhythmia is either marked questionable or is rejected.

FIG. 1 illustrates an embodiment of the invention 100 implemented with an ILR having device body 101 and flexible lead body 102. Signals originating in flexible lead body 102, for example electrical signals, enter device body 101 and are processed by signal analysis module 110 and generally a digitized subset thereof may be stored in memory 120, along with analysis results, arrhythmia detections and/or false arrhythmia detections (or they may be ignored), for example. Embodiments of the invention may be implemented with any other type of implantable device as desired including pacemakers and/or cardioverter/defibrillators.

FIG. 2 illustrates a close-up of flexible lead body 102 having piezoelectric transducer 202 embedded within flexible lead body 102. The piezoelectric transducer 202 is connected to the signal analysis module 110 via feedthrough 201. Flexible lead body 102 also includes sECG electrode 203 that is also connected to signal analysis module 110 via feedthrough 201. The subcutaneous ECG signal or sECG is measured between one electrode at the tip of the lead, i.e., sECG electrode 203 and one electrode on the case on the opposite side of the device, i.e., device body electrode 103, shown as a filled half circle on the left side of device body 101. In alternative embodiments, sECG electrode 203 may be implemented as a tip electrode, wherein another ring electrode may be utilized to obtain the sECG instead of through use of the device body electrode if desired (not shown for brevity).

FIG. 3 illustrates a close-up of feedthrough 201 that provides electrical connections 311, 312 and 313 on the flexible lead body side of feedthrough 201 to the sECG electrode 203 and piezoelectric transducer 202 common and positive respectively, to electrical connections 301, 302 and 303 through feedthrough body 304. Thus, feedthrough 201 enables the internal electronics of the ILR, such as signal analysis module 110 to obtain electrical signals that are generated external to the ILR. Modern piezoelectric transducers are very small and may be produced in different form factors. Since the lead is flexible, any movement of the muscle surrounding the lead will cause bending of the lead. This results in a voltage generated by piezoelectric transducer 202.

FIG. 4 illustrates a logical processing schematic of one embodiment of signal analysis element or module 110 employed by one or more embodiments of the invention. The use of the terms element and module herein are interchangeable and otherwise synonymous and indicate any type of processing object that may include hardware, shared hardware in combination with or without firmware or software. Any type of element may be utilized so long as the element may detect, compare and indicate arrhythmia events within the required time between heartbeats, which requires minimal hardware and/or software complexity based on the relatively low rate of processing utilized as one skilled in the art will appreciate. In one or more embodiments of the invention, a single processing unit may implement all elements or modules or any combination thereof, for example by time division processing of the various signals and outputs.

The signal or data streams from the piezoelectric transducer and the sECG, i.e., the sECG signal and the piezo signal that travel on electrical connections 311 and 312/313 respectively, pass through feedthrough body 304 to electrical connections 301 and 302/303 respectively and are routed into optional amplifiers 401 and 411 respectively and to detection modules 402 and 412 respectively that generate peak markers or detect signal features. The detected movement signal features may include amplitude, signal polarity, waveform or the like or may be detected by comparison with recorded reference signals. Processing in detection modules 402 and 412 (or a single module that time division multiplexes processing for example) may be in the analog or digital domain as desired. The time sequence of the peak markers or signal features are analyzed for coherency in comparator module 403, for example if movement events occur within predefined windows that are in common within N sECG events, then the result of the analysis is forwarded to arrhythmia module 404 for further processing.

Specifically, the time sequences of the sEGC markers are analyzed by arrhythmia detection module 404 and processed, or analyzed to find specific sequences that are indicative of different arrhythmias, for example by comparing event intervals within a sequence of events, or in any other manner. As shown in the embodiment of FIG. 4, a comparator module is located after the detection modules that detect the peaks of the movement markers, and sEGC markers, and in this embodiment, before the arrhythmia detection module. Comparator module 403 identifies the coherency of the movement markers with the sECG markers. If the coherency is above a predefined value, as previously stated for example a number of events in common within predefined windows, i.e., number of events in common over a predefined threshold, then comparator module 403 sends a flag to arrhythmia module 404. In case arrhythmia module 404 has detected a specific arrhythmia while the flag is active this specific arrhythmia is marked as questionable or is rejected by the system.

FIG. 5 illustrates a logical processing schematic of another embodiment of signal analysis module 110 employed by one or more embodiments of the invention. In this sequence both signal streams, the sECG signal and the piezo signal, are processed by arrhythmia detection modules 404 and 414 simultaneously, or within a single arrhythmia detection module in a time division multiplexed manner, which is not shown for brevity. The output is then analyzed by the comparator module for concurrent arrhythmia detection. If both arrhythmia modules for example detect what are thought to be arrhythmia sequences, then the comparator module may determine that there is enough muscle noise to indicate a false positive arrhythmia and thus indicate a false arrhythmia and store the false positive in memory or ignore the arrhythmia indication. Simultaneous detection of an arrhythmia in both signal streams is then indicative of false arrhythmia detection due to muscle activity. In one or more embodiments of the invention, the event may be indicated as questionable, i.e., an event that is potentially indicative of arrhythmia.

In yet another embodiment the piezo signal can be subtracted from the sECG signal, removing the noise artifacts generated by the muscle movement and therefore allows even more specific arrhythmia detection. In one or more embodiments of the invention this may occur after any normalization of signal levels, for example by varying adjusting one or more amplification value for amplifiers 401 and 411 to generate an analog signal by subtracting the piezo signal from the sECG signal. In a discrete embodiment, removal of discrete events, i.e., elimination of any sECG detected events where movement detected events within a predefined time window is also in keeping with the spirit of the invention. In this embodiment, comparator module 403 may be implemented as a subtraction element for example.

Figure 7:
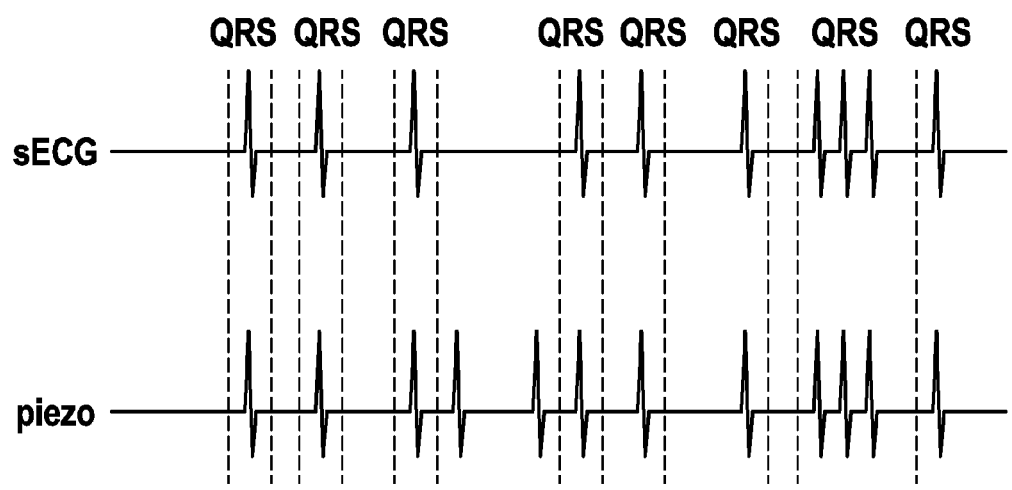
FIG. 7: illustrates an example of rejected arrhythmia detection, wherein the sECG signal and the piezo signal are coherent, which is indicative of a false arrhythmia due to muscle noise.

FIG. 6 illustrates an example of correct arrhythmia detection, wherein the sECG signal and the piezo signal are non-coherent. As shown, voltages associated with movement occur in a non-synchronized manner with respect to QRS events. FIG. 7 illustrates an example of rejected arrhythmia detection, wherein the sECG signal and the piezo signal are coherent, which is indicative of a false arrhythmia due to muscle noise. As shown, voltages associated with movement occur in a synchronized manner with respect to QRS events. In this manner, embodiments of the invention enable high arrhythmia detection specificities through the elimination of false positives associated with muscle movement.

What is claimed is:

1. A electromedical implant configured to improve arrhythmia detections based on active muscle noise detection, comprising:
   a device body comprising
      a signal analysis element coupled with said device body electrode;
      a memory coupled with said signal analysis element;
   an flexible lead body comprising
      a proximal end;
      a distal end;
      at least one electrode situated proximally to said distal end of said flexible lead body wherein said at least one electrode is coupled with said signal analysis element;
      a piezoelectric transducer coupled with said signal analysis element;
   said signal analysis element comprising
      at least one detection element configured to detect peak markers or signal features from said at least one electrode and said piezoelectric transducer;
      wherein said signal analysis element is configured to
         determine if a potential arrhythmia condition exists based on said peak markers or said signal features;
         analyze coherency of said peak markers or said signal features from said at least one electrode and said piezoelectric transducer or between a first potential arrhythmia condition associated with said at least one electrode and a second potential arrhythmia condition associated with said piezoelectric transducer;
            wherein said analyze coherency comprises comparison of said first potential arrhythmia condition with said second potential arrhythmia condition to determine if both said first and said second potential arrhythmia conditions exist concurrently with respect to said at least one electrode and said piezoelectric transducer, and,
         indicate an arrhythmia detection if said coherency is below a predefined threshold and indicate a false arrhythmia detection if said coherency is above said predefined threshold.

2. The electromedical implant of claim 1 wherein said signal analysis element further comprises
   a comparator element coupled with said at least one detection element;
   at least one arrhythmia element coupled with
      a detection element associated with said at least one electrode and
      an output of said comparator element;
      such that said comparator is located between said detection element associated with said at least one electrode and said arrhythmia element;
   wherein
      said comparator element is configured to
         perform said analyze coherency of said peak markers or said signal features from said at least one electrode and said piezoelectric transducer;
      said at least one arrhythmia element is configured to
         perform said determine if a potential arrhythmia condition exists based on said peak markers or said signal features associated with said at least one electrode and
         perform said indicate an arrhythmia detection if said potential arrhythmia condition exists and said coherency is below a predefined threshold and perform said indicate a false arrhythmia detection if said coherency is above said predefined threshold.

3. The electromedical implant of claim 1 wherein said signal analysis element further comprises
   at least one arrhythmia element;
   a comparator element coupled said at least one arrhythmia element;
   wherein
      said at least one arrhythmia element is configured to
         perform said indicate said first and said second potential arrhythmia if said peak markers or said signal features respectively from said at least one electrode and said piezoelectric transducer are indicative of arrhythmia and otherwise indicate no potential arrhythmia detection respectively;
      said comparator element is configured to
         perform said analyze coherency of said first and said second potential arrhythmia associated with said at least one electrode and said piezoelectric transducer and
         perform said indicate an arrhythmia detection if said coherency is below a predefined threshold and perform said indicate a false arrhythmia detection if said coherency is above said predefined threshold.

4. The electromedical implant of claim 1 wherein said analyze coherency further comprises comparison of a number of said peak markers or said signal features from said at least one electrode and from said piezoelectric transducer within predefined time windows to determine if a predefined number of said peak markers or said signal features occur within said predefined time windows over a predefined number of heartbeats.

5. The electromedical implant of claim 1 wherein said device body further comprises a device body electrode wherein said at least one detection element is further configured to detect a voltage differential between said at least one electrode and said device body electrode.

6. The electromedical implant of claim 1 wherein said signal analysis element comprises at least one amplifier coupled with said at least one detection element wherein said at least one amplifier is configured to amplify input voltages from said at least one electrode or said piezoelectric transducer or from said at least one electrode and said piezoelectric transducer.

7. The electromedical implant of claim 1 further comprising:
   a feedthrough configured to physically couple with said device body and said flexible lead body and
      electrically couple said at least one electrode to said signal analysis element and
      electrically couple said piezoelectric transducer to said signal analysis element.

8. The electromedical implant of claim 7 wherein said feedthrough comprises
   a device body side and a flexible lead body side;
   three electrical connections on said flexible lead body; and,
   three electrical connections on said device body side;
   wherein said feedthrough is further configured to electrically couple said at least one electrode to said signal analysis element through a first electrical connection of said three electrical connections on said flexible lead body to a respective first electrical connection of said three electrical connections on said device body side, and wherein said feedthrough is further configured to electrically couple said piezoelectric transducer to said signal analysis element through a second and a third electrical connections of said three electrical connections on said flexible lead body to a respective second and third electrical connections of said three electrical connections on said device body side.

9. The electromedical implant of claim 1 wherein said electromedical implant comprises
an implantable loop recorder or
an implantable pacemaker or
an implantable cardioverter/defibrillator.

10. A electromedical implant configured to improve arrhythmia detections based on active muscle noise detection, comprising:
a device body comprising
a signal analysis element coupled with said device body electrode;
a memory coupled with said signal analysis element;
a device body electrode;
an flexible lead body comprising
a proximal end;
a distal end;
at least one electrode situated proximally to said distal end of said flexible lead body wherein said at least one electrode is coupled with said signal analysis element;
a piezoelectric transducer coupled with said signal analysis element;
said signal analysis element comprising
at least one detection element configured to detect peak markers or signal features from said at least one electrode, said device body electrode and said piezoelectric transducer;
wherein said signal analysis element is configured to
determine if a potential arrhythmia condition exists based on said peak markers or said signal features;
analyze coherency of said peak markers or said signal features from said at least one electrode and said piezoelectric transducer or between a first potential arrhythmia condition associated with said at least one electrode and a second potential arrhythmia condition associated with said piezoelectric transducer;
wherein said analyze coherency comprises comparison of a number of said peak markers or said signal features from said at least one electrode and from said piezoelectric transducer within predefined time windows to determine if a predefined number of said peak markers or said signal features occur within said predefined time windows over a predefined number of heartbeats, and,
indicate an arrhythmia detection if said coherency is below a predefined threshold and indicate a false arrhythmia detection if said coherency is above said predefined threshold.

11. The electromedical implant of claim 10 wherein said signal analysis element further comprises
a comparator element coupled with said at least one detection element;
at least one arrhythmia element coupled with
a detection element associated with said at least one electrode and
an output of said comparator element;
wherein
said comparator element is configured to
perform said analyze coherency of said peak markers or said signal features from said at least one electrode and said piezoelectric transducer;
said at least one arrhythmia element is configured to
perform said determine if a potential arrhythmia condition exists based on said peak markers or said signal features associated with said at least one electrode and
perform said indicate an arrhythmia detection if said potential arrhythmia condition exists and said coherency is below a predefined threshold and perform said indicate a false arrhythmia detection if said coherency is above said predefined threshold.

12. The electromedical implant of claim 10 wherein said signal analysis element further comprises
at least one arrhythmia element;
a comparator element coupled said at least one arrhythmia element;
wherein
said at least one arrhythmia element is configured to
perform said indicate said first and said second potential arrhythmia if said peak markers or said signal features respectively from said at least one electrode and said piezoelectric transducer are indicative of arrhythmia and otherwise indicate no potential arrhythmia detection respectively;
said comparator element is configured to
perform said analyze coherency of said first and said second potential arrhythmia associated with said at least one electrode and said piezoelectric transducer and
perform said indicate an arrhythmia detection if said coherency is below a predefined threshold and perform said indicate a false arrhythmia detection if said coherency is above said predefined threshold.

13. The electromedical implant of claim 10 wherein said analyze coherency further comprises comparison of said first potential arrhythmia condition with said second potential arrhythmia condition to determine if both said first and said second potential arrhythmia conditions exist concurrently with respect to said at least one electrode and said piezoelectric transducer.

14. The electromedical implant of claim 10 wherein said signal analysis element comprises at least one amplifier coupled with said at least one detection element wherein said at least one amplifier is configured to amplify input voltages from said at least one electrode or said piezoelectric transducer or from said at least one electrode and said piezoelectric transducer.

15. The electromedical implant of claim 10 further comprising:
a feedthrough configured to physically couple with said device body and said flexible lead body and
electrically couple said at least one electrode to said signal analysis element and
electrically couple said piezoelectric transducer to said signal analysis element.

16. The electromedical implant of claim 15 wherein said feedthrough comprises
a device body side and a flexible lead body side;
three electrical connections on said flexible lead body; and, three electrical connections on said device body side;
wherein said feedthrough is further configured to electrically couple said at least one electrode to said signal analysis element through a first electrical connection of said three electrical connections on said flexible lead body to a respective first electrical connection of said three electrical connections on said device body side, and
wherein said feedthrough is further configured to electrically couple said piezoelectric transducer to said signal analysis element through a second and a third electrical connections of said three electrical connections on said flexible lead body to a respective second and third electrical connections of said three electrical connections on said device body side.

17. The electromedical implant of claim 10 wherein said electromedical implant comprises
an implantable loop recorder or
an implantable pacemaker or
an implantable cardioverter/defibrillator.

18. A electromedical implant configured to improve arrhythmia detections based on active muscle noise detection, comprising:
a device body comprising
a signal analysis element coupled with said device body electrode;
a memory coupled with said signal analysis element;
a device body electrode;
an flexible lead body comprising
a proximal end;
a distal end;
at least one electrode situated proximally to said distal end of said flexible lead body wherein said at least one electrode is coupled with said signal analysis element;
a piezoelectric transducer coupled with said signal analysis element;
a feedthrough configured to physically couple with said device body and said flexible lead body and
electrically couple said at least one electrode to said signal analysis element and
electrically couple said piezoelectric transducer to said signal analysis element;
wherein said feedthrough comprises
a device body side and a flexible lead body side;
three electrical connections on said flexible lead body; and,
three electrical connections on said device body side;
wherein said feedthrough is further configured to electrically couple said at least one electrode to said signal analysis element through a first electrical connection of said three electrical connections on said flexible lead body to a respective first electrical connection of said three electrical connections on said device body side, and
wherein said feedthrough is further configured to electrically couple said piezoelectric transducer to said signal analysis element through a second and a third electrical connections of said three electrical connections on said flexible lead body to a respective second and third electrical connections of said three electrical connections on said device body side;
said signal analysis element comprising
at least one detection element configured to detect peak markers or signal features from said at least one electrode, said device body electrode and said piezoelectric transducer;
at least one amplifier coupled with said at least one detection element wherein said at least one amplifier is configured to amplify input voltages from said at least one electrode or said piezoelectric transducer or from said at least one electrode and said piezoelectric transducer;
wherein said signal analysis element is configured to
determine if a potential arrhythmia condition exists based on said peak markers or said signal features;
analyze coherency of said peak markers or said signal features from said at least one electrode and said piezoelectric transducer or between a first potential arrhythmia condition associated with said at least one electrode and a second potential arrhythmia condition associated with said piezoelectric transducer wherein said analyze coherency comprises
comparison of a number of said peak markers or said signal features from said at least one electrode and said piezoelectric transducer within predefined time windows to determine if a predefined number of said peak markers or said signal features occur within said predefined time windows over a predefined number of heartbeats or
comparison of said first and second potential arrhythmia conditions to determine if both said first and said second potential arrhythmia conditions exist concurrently with respect to said at least one electrode and said piezoelectric transducer;
wherein said electromedical implant comprises an implantable loop recorder or an implantable pacemaker or an implantable cardioverter/defibrillator.

19. The electromedical implant of claim 18 wherein said signal analysis element further comprises
a comparator element coupled with said at least one detection element;
at least one arrhythmia element coupled with
a detection element associated with said at least one electrode and
an output of said comparator element;
wherein
said comparator element is configured to
perform said analyze coherency of said peak markers or said signal features from said at least one electrode and said piezoelectric transducer;
said at least one arrhythmia element is configured to
perform said determine if a potential arrhythmia condition exists based on said peak markers or said signal features associated with said at least one electrode and
perform said indicate an arrhythmia detection if said potential arrhythmia condition exists and said coherency is below a predefined threshold and perform said indicate a false arrhythmia detection if said coherency is above said predefined threshold.

20. The electromedical implant of claim 18 wherein said signal analysis element further comprises
at least one arrhythmia element;
a comparator element coupled said at least one arrhythmia element;
wherein
said at least one arrhythmia element is configured to
perform said indicate said first and said second potential arrhythmia if said peak markers or said signal features respectively from said at least one electrode and said piezoelectric transducer are indicative of arrhythmia and otherwise indicate no potential arrhythmia detection respectively;

said comparator element is configured to
perform said analyze coherency of said first and said second potential arrhythmia associated with said at least one electrode and said piezoelectric transducer and
perform said indicate an arrhythmia detection if said coherency is below a predefined threshold and perform said indicate a false arrhythmia detection if said coherency is above said predefined threshold.

\* \* \* \* \*